United States Patent [19]

Boden

[11] 4,399,063
[45] Aug. 16, 1983

[54] PRINS REACTION PRODUCTS OF DIISOBUTYLENE, DERIVATIVES THEREOF, ORGANOLEPTIC USES THEREOF AND PROCESSES FOR PREPARING SAME

[75] Inventor: Richard M. Boden, Monmouth Beach, N.J.

[73] Assignee: International Flavors & Fragrances Inc., New York, N.Y.

[21] Appl. No.: 391,595

[22] Filed: Jun. 24, 1982

Related U.S. Application Data

[62] Division of Ser. No. 280,683, Jul. 6, 1981.

[51] Int. Cl.$^3$ .............................................. C11B 9/00
[52] U.S. Cl. .............................................. 252/522 R
[58] Field of Search ........................ 252/522 R; 5/451

[56] References Cited

U.S. PATENT DOCUMENTS

| | | | |
|---|---|---|---|
| 3,959,396 | 5/1976 | Ochsner et al. | 252/522 R X |
| 4,192,781 | 3/1980 | Näf | 252/522 R |
| 4,336,164 | 6/1982 | Boden | 252/522 R |
| 4,359,412 | 11/1982 | Boden | 252/522 R |
| 4,374,053 | 2/1983 | Klemarczyk et al. | 252/522 R |

FOREIGN PATENT DOCUMENTS

| | | |
|---|---|---|
| 2108805 | 8/1971 | Fed. Rep. of Germany . |
| 465941 | 9/1976 | U.S.S.R. .......... 252/522 R |

OTHER PUBLICATIONS

Hirai et al., CA 65:2114f, (1966).
Guillemonat, CA 33:4579$^6$ (1939).
Hariel, CA 72:24504e, (1970).
Honkanen et al., CA 72:120243q, (1970).

*Primary Examiner*—Thomas A. Waltz
*Attorney, Agent, or Firm*—Arthur L. Liberman

[57] ABSTRACT

Described for augmenting or enhancing the aroma or taste of consumable materials including perfume compositions, perfumed articles (e.g., solid or liquid anonionic, cationic, nonionic, and zwitterionic detergents), colognes, foodstuffs, chewing gums, toothpastes, chewing tobaccos and medicinal products are certain Prins reaction products and derivatives thereof of diisobutylene defined according to the generic structures:

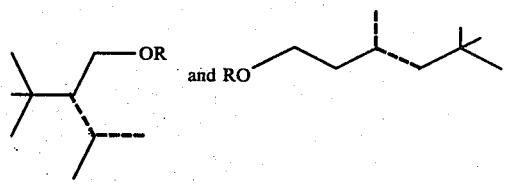

wherein one of the dashed lines represents a carbon-carbon double bond and the other of the dashed lines represent a carbon-carbon single bond and wherein "R" represents hydrogen or acetyl.

3 Claims, 5 Drawing Figures

GLC PROFILE FOR EXAMPLE I.

IR SPECTRUM FOR EXAMPLE I.

GLC PROFILE FOR EXAMPLE II.

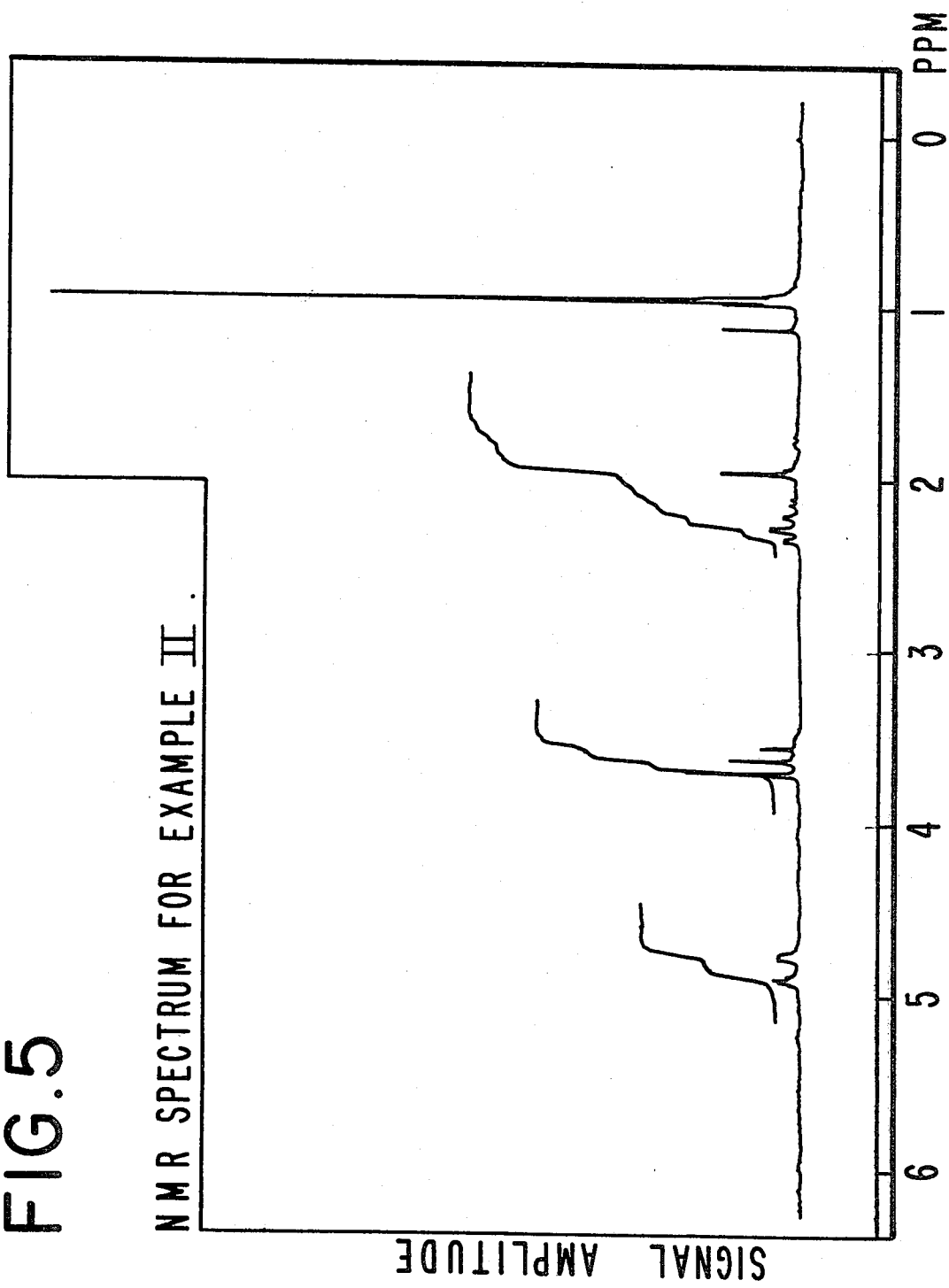

PRINS REACTION PRODUCTS OF DIISOBUTYLENE, DERIVATIVES THEREOF, ORGANOLEPTIC USES THEREOF AND PROCESSES FOR PREPARING SAME

This is a divisional of application Ser. No. 280,683, filed July 6, 1981.

BACKGROUND OF THE INVENTION

The present invention relates to Prins reaction products of diisobutylene and derivatives thereof defined according to the genera:

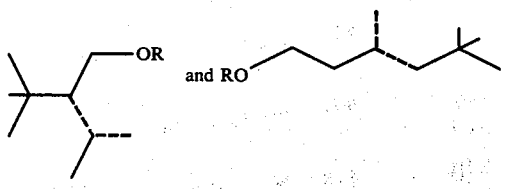

wherein one of the dashed lines represents a carbon-carbon double bond and the other of the dashed lines represent a carbon-carbon single bond, and wherein "R" represents hydrogen or acetyl and to novel compositions using such Prins reaction products or derivatives thereof to augment or enhance the flavor and/or aroma of consumable materials or to impart flavor and/or aroma to consumable materials.

There has been considerable work performed relating to substances which can be used to impart (modify, augment or enhance) flavors and fragrances to (or in) various consumable materials. These substances are used to diminish the use of natural materials, some of which may be in short supply, and to provide more uniform properties in the finished product.

Spicy, cumin oil-like, green and herbaceous aroma and taste nuances are particularly desirable for use in foodstuff flavors, chewing gum flavors, toothpaste flavors, medicinal product flavors and chewing tobacco flavors. These aroma and taste nuances are particularly useful in curry flavors for foodstuffs and spice flavors for foodstuffs.

Spicy, clove-like, cinnamon-like, floral and minty aromas with warm woody undertones are particularly desirable for perfume aromas and for perfumed article aromas and for aromas or colognes.

U.S. Pat. No. 2,315,046 discloses the use as ingredients in perfumery of certain acylated olefins, which olefins have structures such as:

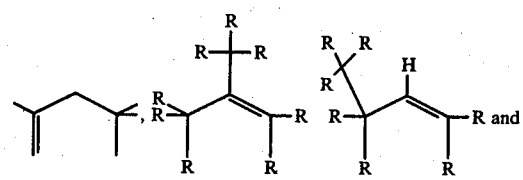

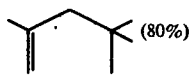

and

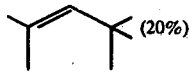

These materials are prepared interalia from commercial diisobutylene according to the reaction:

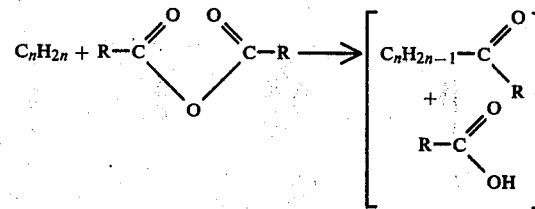

wherein n is 3 or more, and R represents a hydrocarbon radical. Branched unsaturated alpha-beta ketones were known prior to that, for example in U.S. Pat. No. 2,246,032, issued on June 17, 1941, disclosing compounds having the generic structure:

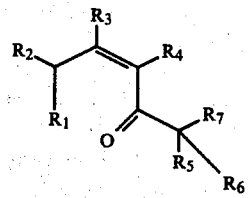

wherein $R_1$–$R_7$ may be any member of a group consisting of hydrogen, aliphatic and cyclo praffinic.

Also, claimed in U.S. Pat. No. 2,315,046 are compounds having the structures:

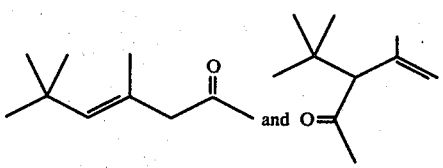

In addition, U.S. Pat. No. 2,463,742 discloses the reaction:

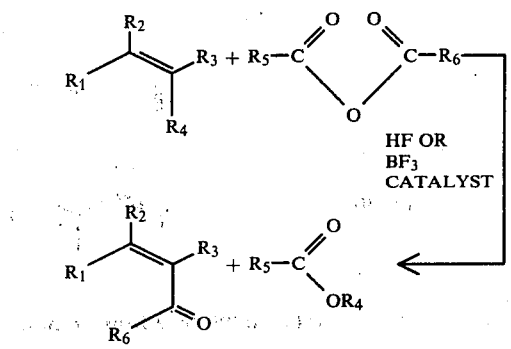

Perfumery compounds are known to have been produced using the Prins reaction. Thus, the paper entitled "The Olefin-Aldehyde Condensation/The Prins Reaction" by Arundale and Mikeska, Chem. Reviews, 51, 505-55 1952, discloses the reaction to form Nopol acetate, thusly:

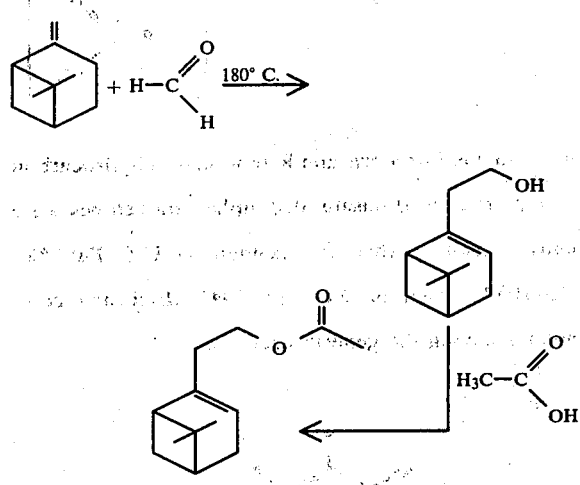

wherein in the reaction, when glacial acetic acid is added to the reaction mass, the Nopol acetate is formed; yet without the use of glacial acetaic acid, Nopol itself is formed.

U.S. Pat. No. 4,100,110 issued on July 11, 1978 (Class 252, Subclass 522) discloses compounds for use in perfumery which are obtained by performing a Prins reaction on longifolene including primary and secondary alcohols, their esters and corresponding aldehydes and ketones. Specifically, in Example 1, column 7 of U.S. Pat. No. 4,100,110 discloses the preparation of compounds having the structures:

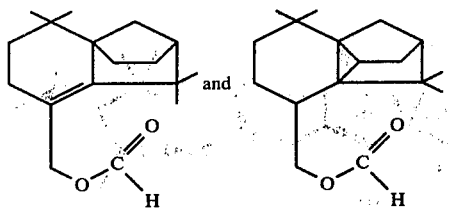

for use in perfumery as a result of their cedarwood-vetiver aroma.

The compounds of the prior art and processes of the prior art are different in kind and yield materials having organoleptic properties different in kind from the compounds of the instant invention.

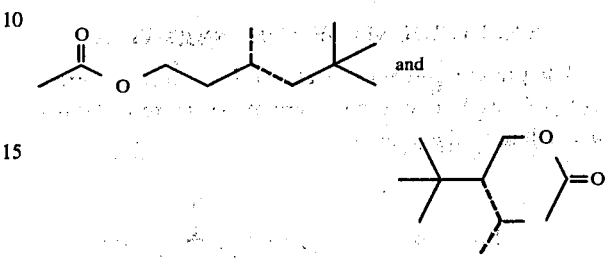

wherein in the mixture in each of the molecules one of the dashed lines represents a carbon-carbon double bond and the other of the dashed lines represents a carbon-carbon single bond.

Figure 2:
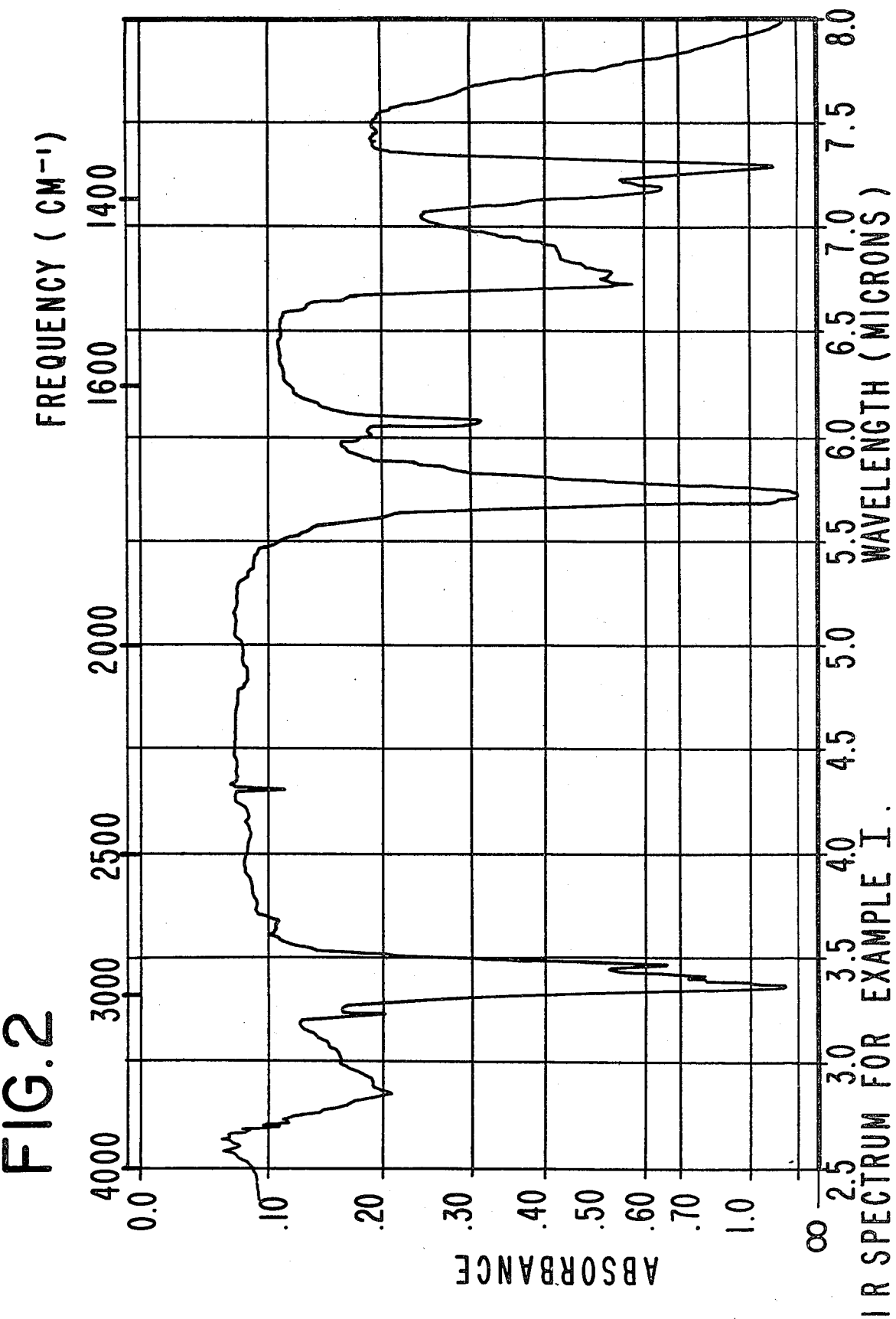

FIG. 2 is the infra-red spectrum for the reaction product of Example I containing a mixture of compounds defined according to the structures:

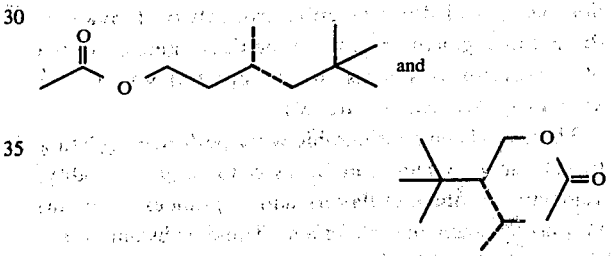

wherein in the mixture in each of the molecules one of the dashed lines represents a carbon-carbon double bond and the other of the dashed lines represents a carbon-carbon single bond.

Figure 3:
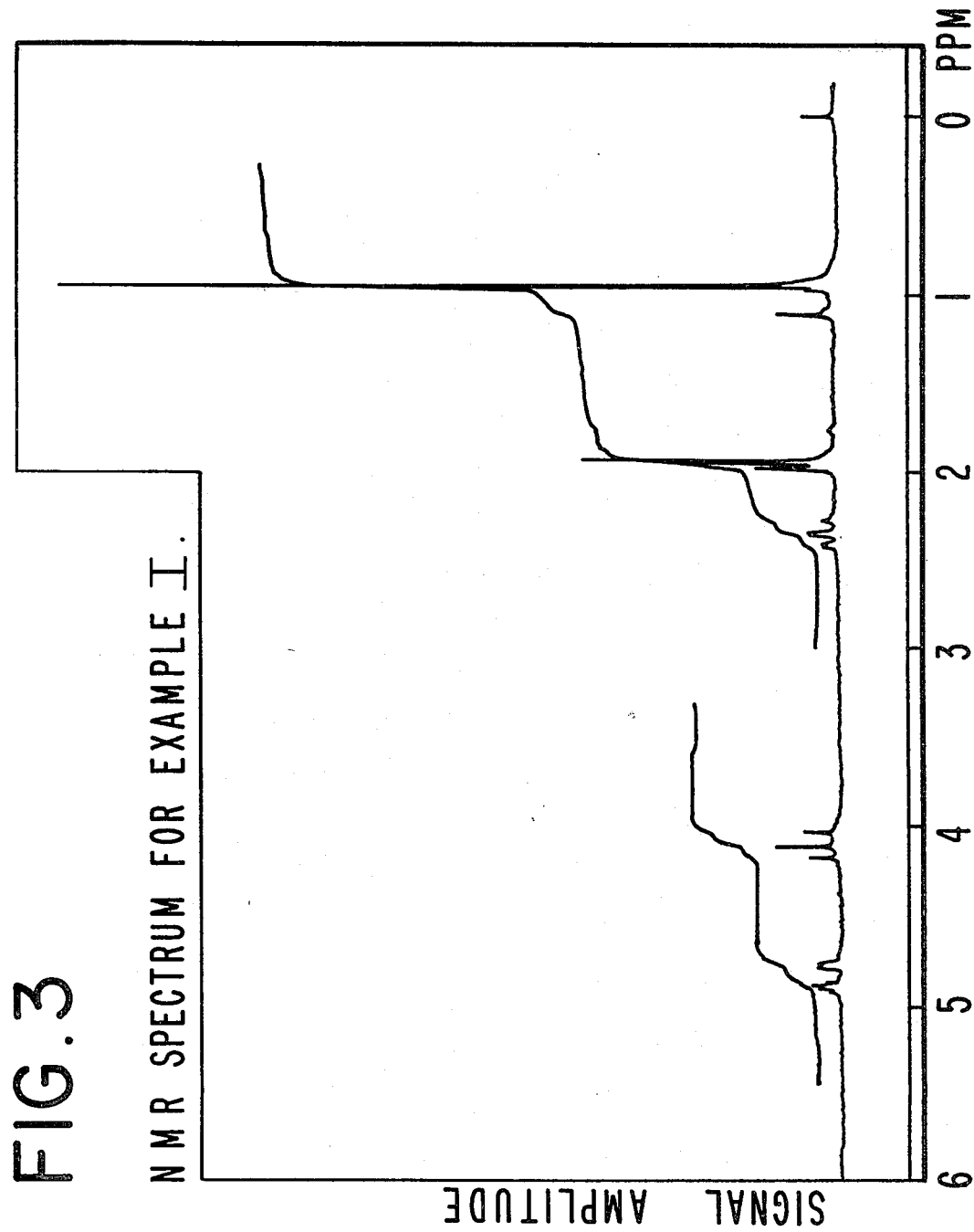

FIG. 3 is the NMR spectrum for the reaction product of Example I containing a mixture of compounds defined according to the structures:

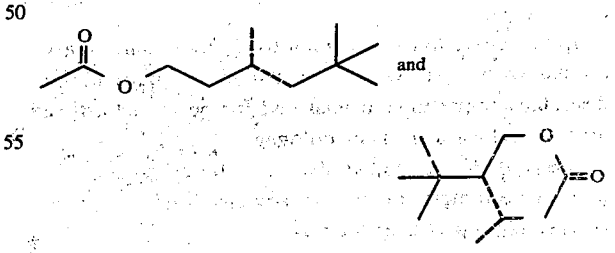

wherein in each of the molecules of the compound one of the dashed lines represents a carbon-carbon double bond and the other of the dashed lines represents a carbon-carbon single bond.

Figure 4:
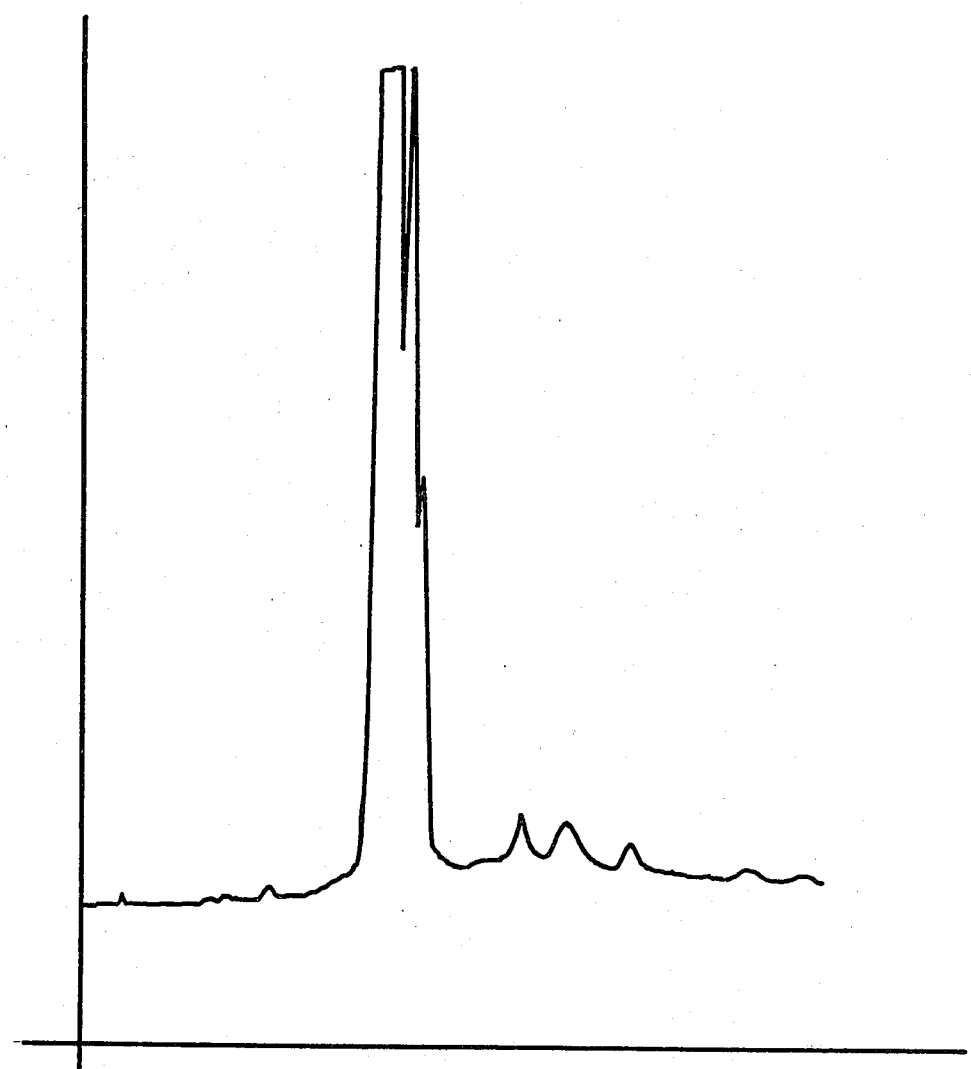

FIG. 4 is the GLC profile for the reaction product of Example II containing a mixture of compounds defined according to the structures:

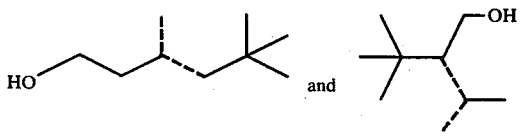

wherein in the mixture in each of the molecules, one of the dashed lines is a carbon-carbon double bond and the other of the dashed lines is a carbon-carbon single bond.

FIG. 5 is the NMR spectrum for the reaction product of Example II containing a mixture of compounds defined according to the generic structures:

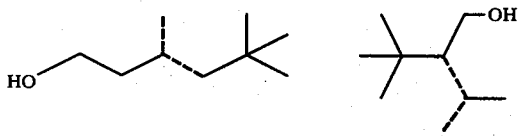

wherein in the mixture one of the dashed lines is a carbon-carbon double bond, and the other of the dashed lines is a carbon-carbon single bond.

THE INVENTION

It has now been discovered that novel solid and liquid foodstuff, chewing gum, medicinal products, toothpaste and chewing tobacco compositions and flavorings therefore having spicy, cumin oil-like, green and herbaceous aroma and taste nuances; as well as novel, solid and liquid perfume, perfumed article and cologne compositions and aromatizing compositions therefore having spicy, clove, cinnamon-like, floral and minty aroma profiles with warm woody undertones; and novel solid and liquid smoking tobacco, substitute smoking tobacco, smoking tobacco article and substituted smoking tobacco article compositions and aroma and flavoring compositions therefore having clove-like and minty aroma and taste nuances both prior to and on smoking in the mainstream and the sidestream may be provided by the utilization of one or more Prins reaction products of diisobutyllene or derivatives thereof defined according to one of the generic structures:

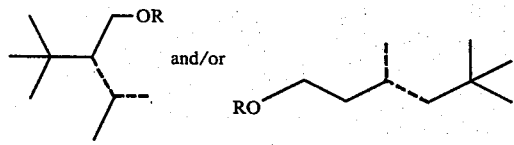

wherein one of the dashed lines represents a carbon-carbon double bond, and the other of the dashed lines represents a carbon-carbon single bond and wherein, "R" represents hydrogen or acetyl.

The compounds defined according to the generic structures:

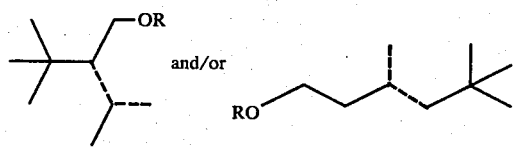

wherein one of the dashed lines represents a carbon-carbon double line, and the other of the dashed lines represents a carbon-carbon single bond and "R" represents hydrogen or acetyl may be prepared by first dimerizing isobutylene according to the teaching of U.S. Pat. No. 2,315,046 or according to the teaching of Japanese Kokai No. 79,157,510 published on Dec. 12, 1979 (abstracted in Chem Abstracts Vol. 93:25885a) wherein the dimerization of the isobutylene is indicated to take place in the presence of alkylaluminum chloride catalysts such as ethyl aluminum dichloride.

The resulting mixture of dimers of isobutylene may be separated and the individual compounds may be used as is or the resulting mixture may be used in the next reaction wherein the dimer or mixture of dimers is subjected to a Prins reaction with acetic anhydride and either (i) formaldehyde, or (ii) a formaldehyde source such as formalin, paraformaldehyde or trioxane in the presence of (iii) a Lewis acid such as boron trifluoride, boron triflouride etherate, stannic chloride, ethyl aluminum dichloride or diethyl aluminum chloride according, for example, to the reaction:

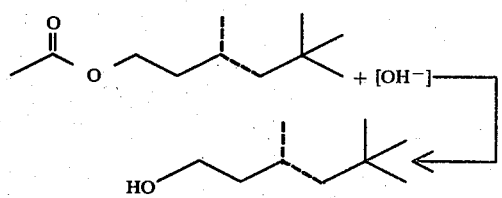

(wherein, one of the dashed lines represents a carbon-carbon double bond and the other of the dashed lines represents a carbon-carbon single bond) and the structure:

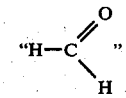

represents formaldehyde itself or a formaldehyde source as such trioxane having the structure:

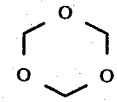

or paraformaldehyde having the structure:

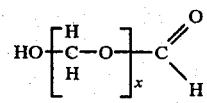

(wherein, "x" represents an integer of from 1 up to 20 or higher).

The resulting product is a mixture defined according to the structures:

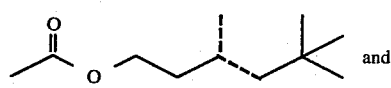 and

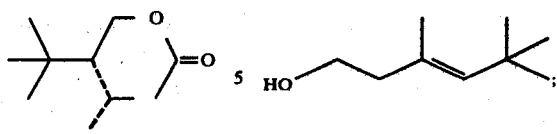

wherein, in the mixture in each of the molecules one of the dashed lines is a carbon-carbon double bond and the other of the dashed lines is a carbon-carbon single bond or individual compounds defined according to the structures:

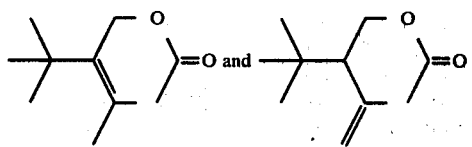

depending upon whether the starting material, the diisobutylene, is a mixture defined according to the structure:

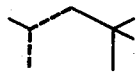

(defining a mixture wherein in the mixture one of the dashed lines is a carbon-carbon double bond and the other of the dashed lines is a carbon-carbon single bond) or a single compound having one of the structures:

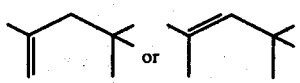

The resulting compounds may be used "as is" for their organoleptic properties; that is, for their spicy and clove aroma nuances in perfumery, or their spicy and clove nuances as flavorants for foodstuffs or their spicy and clove nuances as flavorants, or aromatizers for smoking tobacco and smoking tobacco articles, or the resulting acetates may be hydrolyzed using aqueous base, e.g., sodium hydroxide, potassium hydroxide, lithium hydroxide, sodium carbonate, potassium carbonate or lithium carbonate whereby alcohols defined according to one of the structures:

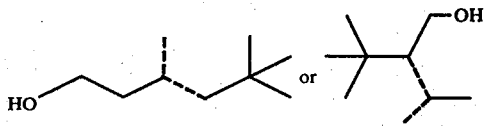

(indicating a mixture wherein in the mixture in one of the molecules one of the dashed lines is a carbon-carbon double bond and the other of the dashed lines is a carbon-carbon single bond) or compounds defined according to one of the structures:

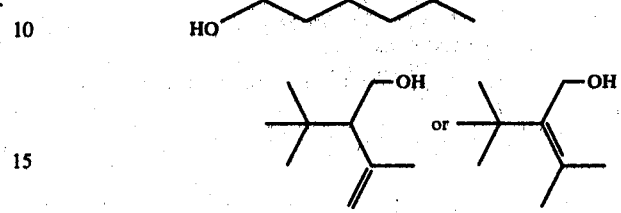

depending on whether the acetate hydrolyzed is defined respectfully according to one of the structures:

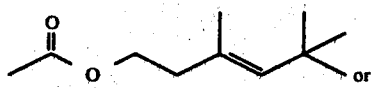

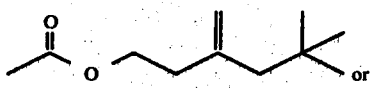

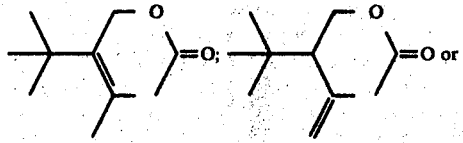

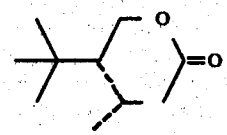

wherein the structures:

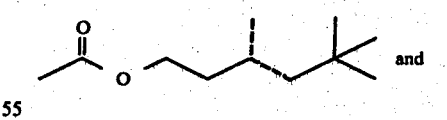

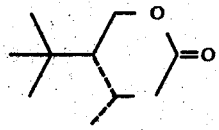

defines a mixture wherein in the mixture in one of the molecules one of the dashed lines represents a carbon-carbon double bond and each of the other of the dashed lines represent carbon-carbon single bonds. This hydrolysis reaction is exemplified according to the following reaction:

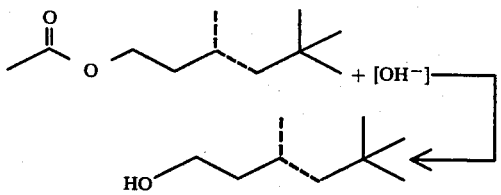

wherein, one of the dashed lines represents a carbon-carbon double bond and the other of the dashed lines represent carbon-carbon single bonds.

The mole ratio of diisobutylene:formaldehyde (as paraformaldehyde or as trioxane) may vary from about 1:2 up to about 2:1 with a preferred mole ratio of about 1:1. The mole ratio of acyl anhydride:diisobutylene may vary from about 1:1 up to about 2:1 acyl anhydride:-diisobutylene with a preferred mole ratio of 1.4–1.5:1 of acyl anhydride:diisobutylene. The concentration of diisobutylene in the reaction mass is preferably from about 1 mole per liter up to about 5 moles per liter.

The concentration of Lewis acid in the reaction mass may vary from about 0.01 moles per liter up to about 0.5 moles per liter.

The reaction temperature may vary from about 50° C. up to about 150° C. depending on the pressure above the reaction mass and depending upon the time desired to complete the reaction for a given particular yield. When higher temperatures are used, the time of reaction required for completion is shorter, however, the yield is lower and the quantity of by-product formed is greater. The most desirable reaction temperature varies between 80° and 110° C. It is most preferable to carry out the reaction at atmospheric pressure. Higher reaction pressures or lower reaction pressures do not give rise to a higher yield or higher conversion rate.

At the end of the reaction, the reaction mass may be "worked-up" in the usual way by means of, for example, distillation or chromatographic separation, e.g., commercial high-pressure liquid chromatography.

In carrying out the hydrolysis reaction the mole ratio of ester to alkali metal hydroxide, e.g., potassium hydroxide, sodium hydroxide or lithium hydroxide, may vary from about 1:2 up to about 2:1 with an excess of alkali metal hydroxide being preferred. That is, it is preferred that the mole ratio of alkali metal hydroxide:ester be about 2:1. It is preferred that the hydrolysis be carried out using highly concentrated base, e.g., from about 30% up to about 50% concentration. The concentration of ester in the reaction mass may vary from about 1 up to about 8 moles per liter with a concentration of 2–3 moles per liter of ester being preferred. The concentration of caustic is preferably double the concentration of ester. Thus, the concentration of caustic may vary from about 3 moles per liter up to about 10 moles per liter with a preferred concentration of caustic being about 5 moles per liter. The temperature of hydrolysis is preferably between about 50° C. Up to about 80° C. with a hydrolysis temperature of 65° C. being preferred, at atmospheric pressure. Pressures above atmospheric pressure or below atmospheric pressure may be used for the hydrolysis reaction but using higher or lower pressures does not give rise to any advantage insofar as yield or conversion per unit time is concerned. Indeed, most economically, the reaction pressure for this hydrolysis reaction is preferably 1 atmosphere.

At the end of the hydrolysis reaction, the reaction mass may be appropriately worked up as by pH adjustment and fractional distillation thereby yielding the unsaturated alcohol.

When the Prins reaction products of diisobuytlene and derivatives thereof of my invention are used as food flavors adjuvants, or toothpaste flavor adjuvants, or chewing gum flavor adjuvants, formulating the product composition will also serve to augment or enhance the organoleptic characteristics of the ultimate foodstuff, chewing gum, medicinal product or toothpaste treated therewith.

The term "augment" in its various forms is used herein to mean the supplying, modifying or imparting of a flavor or aroma characteristic, note or nuance to an otherwise bland, relatively tasteless or non-odorous substance or modifying an existing flavor or aroma characteristic where the natural flavor is deficient in some regard, or supplementing the existing flavor or aroma impression to modify its quality, character, taste or aroma.

The term "enhance" is used herein to mean the intensification of a flavor or aroma characteristic or note without the modification of the quality thereof. Thus, "enhancement" of a flavor or aroma means that the enhancement agent does not add any additional flavor note or nuance.

As used herein, the term "foodstuff" includes both solid and liquid ingestible materials which usually do, but need not, have nutritional value. Thus, foodstuffs includes soups, convenience foods, beverages, dairy products, candies, vegetables, cereals, soft drinks, snacks and the like.

As used herein, the term "medicinal products" includes both solids and liquids which are ingestible non-toxic materials which have medicinal value such as cough syrups, cough drops, aspirin and chewable medicinal tablets.

The term "chewing gum" is intended herein to be a foodstuff which is a composition which comprises a substantially water-insoluble, chewable plastic gum base such as chicle, or substitutes therefor, including jelutong, guttakay rubber or certain comestible natural or synthetic resins or waxes. Incorporated with the gum base in admixture therewith may be plasticizers or softening agents, e.g., glycerine; and a flavoring composition which incorporates one or more of the unsaturated branched ketones of our invention, and, in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is required that any such material be "ingestibly acceptable", and thus non-toxic or otherwise non-deleterious, particularly from an organoleptic standpoint whereby the ultimate flavor and/or aroma of the consumable material used does not cause the consumable material to have unacceptable aroma and taste nuances.

It is a further requirement that such material be organoleptically compatible with the foodstuff with which it is used so that the flavor and aroma nuances of such material, taken together with the flavor and aroma nuances of the foodstuff (as a whole) give rise to a harmoniously aesthically pleasing aroma and taste profile. Such materials, in general, may be characterized as flavoring adjuvants or vehicles comprising broadly, stabilizers, thickeners, surface active agents, conditioners, other flavorants and flavor intensifiers.

Stabilizer compounds include preservatives, e.g., sodium chloride, antioxidants, e.g., calcium and sodium ascorbate, ascorbic acid, butylated hydroxyanisole (mixture of 2- and 3-tertiary-butyl-4-hydroxyanisole), butylated hydroxy toluene (2,6-di-tertiarybutyl-4-methyl phenol), propyl gallate and the like and sequestrants, e.g., citric acid.

Thickener compounds include carriers, binders, protective colloids, suspending agents, emulsifiers and the like, e.g., agar agar, carrageenan, cellulose and cellulose derivatives such as carboxymethyl cellulose and methyl cellulose; natural and synthetic gums such as gum arabic, gum tragacanth; gelatin, proteinaceous materials, lipids; carbohydrates, starches, pectins, and emulsifiers, e.g., mono-and diglycerides of fatty acids, skim milk powder, hexoses, pentoses disaccharides, e.g., sucrose corn syrup and the like.

Surface active agents include emulsifying agents, e.g., fatty acids such as, palmitic acid, myristic acid and the like, mono- and diglycerides of fatty acids, lecithin, defoaming and flavor-dispersing agents such as sorbitan monostearate, potassium monostearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like colorants, e.g., carminic acid, cochineal, tumeric, curcumin and the like; firming agents such as aluminum sodium sulfate, calcium chloride and calcium gluconate; texturizers, anticaking agents, e.g., aluminum calcium sulfate and tribasic calcium phosphate; enzymes; yeast foods, e.g., calcium lactate and calcium sulfate; ntrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, 2-methyl-cis-3-pentenoic acid; ketones and aldehydes, e.g., octanal, n-decanal, acetaldehyde, acetophenone, acetone, acetyl methyl carbinol, acrolein, n-butanal, crotonal, diacetyl, 2-methyl butanal, beta, beta-dimethyl-acrolein, methyl-n-amyl ketone, n-hexanal, 2-hexenal, isopentanal, hydrocinnamic aldehyde, cis-3-hexenal, 2-heptenal, nonyl aldehyde, citral 4-(p-hydroxyphenyl)-2-butanone, alpha-ionone, 2-methyl-3-butanone, benzaldehyde, damascone, damascenone, acetophenone, 2-heptanone, o-hydroxyacetophenone, 2-methyl-2-hepten-6-one, 2-octanone, 2-undecanone,, 3-phenyl-4-pentenal, 2-phenyl-2-hexenal, 2-phenyl-2-pentenal, furfural, 5-methyl furfural, cinnamaldehyde, β-cyclohomocitral, 2-pentanone, 2-pentenal and propanal; alcohols such as 1-butanol, benzyl alcohol, 1-borneol, trans-2-buten-1-ol, ethanol, geraniol, 1-hexanol, 2-heptanol, trans-2-hexenol-1, cis-3-hexen-1-01, 3-methyl-3-buten-1-ol, 1-pentanol, 1-penten-3-ol, p-hydroxyphenyl-2-ethanol, isoamyl alcohol, fenchyl alcohol, isofenchyl alcohol, phenyl-2-ethanol, α-terpineol, cis-trpineol hydrate, eugenol, linalool, 2-heptanol, acetoin; esters such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl α-methylbutyrate, ethyl propionate, ethyl salicylate, trans-2-hexenyl acetate, hexyl acetate, 2-hexenyl butyrate, hexyl butyrate, isoamyl acetate, isopropyl butyrate, dimethyanthranilate, methyl acetate, methyl butyrate, methyl caproate, methyl isobutyrate, α-methylphenylglycidate, ethyl succinate, isobutyl cinnamate, cinnamyl formate, methyl cinnamate and terpinenyl acetate; hydrocarbons such as dimethyl naphthalene, dodecane, methyl diphenyl, methyl naphthalene, myrcene, cadinene, limonene, naphthalene, octadecane, tetradecane, tetramethyl naphthalene, tridecane, trimethyl naphthalene, undecane, caryophyllene, 1-phellandrene, p-cymene, 1-α-pinene; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, α-methyl-3-ethylpyrazine, tetramethylpyrazine, trimethylpyrazine; essential oils, such as jasmine absolute, cassia oil, cinnamon bark oil, rose absolute, orris absolute, lemon essential oil, orange essential oil, grapefruit essential oil, Bulgarian rose, oil of dill, oil of caraway, oil of spearmint, yara yara and vanila; lactones such as gammanonalactone; sulfides, e.g., methyl sulfide and other materials such as maltol, and acetals (e.g., 1,1-diethoxyethane, 1,1-dimethoxyethane and dimethoxymethane).

The specific flavoring adjuvants selected for use may be either solid or liquid depending upon the deisred physical form of the ultimate product, i.e., foodstuff, whether simulated or natural, and should, in any event, (i) be organoleptically compatible with Prins reaction products of diisobutylene and derivatives thereof of our invention by not covering or spoiling the organoleptic properties (aroma and taste) thereof; (ii) be non-reactive with the Prins reaction products of diisobutylene and derivatives thereof of our invention; and (iii) be capable of providing an environment in which the Prins reaction products of diisobutylene and derivatives thereof of our invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, augmented or enhanced. In contradistinction, in the preparation of solid products, e.g., simulated foodstuffs, ingredients capable of providing normally solid compositions should be selected such as various cellulose derivatives.

As well be appreciated by those skilled in the art, the amount of Prins reaction products of diisobutylene and derivatives thereof of our invention employed in a particular instance can vary over a relatively wide range, depending upon the desired organoleptic effects to be achieved. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected be effective, i.e., sufficient to augment or enhance the organoleptic characteristics of the parent composition, whether foodstuff per se, chewing gum per se, medicinal product per se, toothpaste per se, or flavoring composition.

The use of insufficient quantities of Prins reaction products of diisobutylene and derivatives thereof of our invention will, of course, substantially vitiate any possibility of obtaining the desired results while excess quantities prove needlessly costly and, in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of Prins reaction products of diisobutylene and derivatives thereof of our invention ranging from a small but effective amount, e.g., 0.02 parts per million (ppm) up to about 50 parts per million (ppm) based on total composition are suitable. Concentrations in excess of the maximum quantity stated are not normally recommended, since they fail to provide commensurate enhancement of organoleptic properties. In those instances, where the Prins reaction products of diisobutylene and derivatives thereof of our invention is added to the foodstuff as an integral component of a flavoring composition, it is, of course, essential that the total quantity of flavoring composition employed be sufficient to yield an effective Prins reaction products of diisobutylene and derivatives thereof of our invention concentration in the foodstuff product.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the unsaturated branched ketones of our invention with, for example, gum arabic, gum tragacanth, carrageenan and the like, and thereafter spray-drying the resultant mixture whereby to obtain the particulate solid product. Pre-prepared flavor mixes in powder form, e.g., a fruit-flavored powder mixes are obtained by mixing the dried solid components, e.g., starch, sugar and the like and the unsaturated branched ketones of our invention in a dry blender until the requisite degree of uniformity is achieved.

It is presently preferred to combine with the Prins reaction products of diisobutylene and derivatives thereof of our invention, the following adjuvants:

Oil of dillweed
Oil of garlic
Oil of capsicum
Oil of cassia
Oil of cloves
Oil of pimenta berries
Oil of mustard
Oil of bay leaves
L-carvone
D-carvone
Spearmint oil
Cumin aldehyde
Cinamaldehyde As olfactory agents, the Prins reaction products of diisobutylene and derivatives thereof, taken alone or in admixture of my invention can be formulated into when the Prins reaction product of diisobutylene and derivatives thereof of our invention are used as food flavor adjuvants, or used as components of a "perfume composition" or can be used as components of a "perfumed article", or the perfume composition may be added to perfumed articles.

The term "perfume composition" is used herein to mean a mixture of organic compounds including, for example, alcohols, aldehydes, ketones, nitriles, ethers, lactones, natural essential oils, synthetic essential oils and hydrocarbons other than the Prins reaction products of diisobutylene and derivatives thereof of this invention which are admixed so that the combined odors of the individual components produce a pleasant or desired fragrance. Such perfume compositions usually contain (a) the main note or the "bouquet" or foundation stone of the composition; (b) modifiers which round off and accompany the main note; (c) fixtures which include odorous substances which lend a particular note to the perfume throughout all stages of evaporation, and substances which retard evaporation; and (d) top notes which are usually low boiling, fresh-smelling materials.

In perfume compositions, the individual component will contribute its particular olfactory characteristics, but the overall effect of the perfume composition will be the sum of the effects of each of the ingredients and in certian instances, a synergistic effect as a result of the addition of certain ingredients. Thus, the individual compounds of this invention, or mixtures thereof, can be used to alter the aroma characteristics of a perfume composition, for example, by highlighting or moderating the olfactory reaction contributed by another ingredient in the composition.

The amount of the Prins reaction products of diisobutylene and derivatives thereof of this invention will be effective in perfume compositions depends on many factors, including the other ingredients, their amounts and the effects which are desired. It has been found that perfume compositions containing as little as 0.05% of the Prins reaction products of diisobutylene and derivatives thereof of this invention, or even less, can be used to impart an interesting, herbaceous, piney and woody aroma to soaps, liquid or solid anionic, cationic, nonionic or zwitterionic detergents, cosmetics, cosmetic powders, liquid and solid fabric softeners, dryer-added fabric softener articles, (e.g., BOUNCE ® a registered trademark of the Procter & Gamble Company of Cincinnatio, Ohio), optical brightener compositions and other products. The amount employed can range up to 70% or even higher, and will depend on considerations of cost, nature of the end product, and the effect desired on the finished product and particular fragrance sought. Thus, for example, when fragrancing liquid bleach compositions containing alkalihypochlorite such as, for example, sodium hypochlorite, for example CLOROX ®, (registered trademark of Clorox, Inc.). The amount employed can be as high as 100% of the fragrance involved in the liquid bleach. Indeed, a distinctive aspect of our invention is the use of one or more of the Prins reaction products of diisobutylene and derivatives thereof of this invention in a stable liquid bleach composition.

The Prins reaction products of diisobutylene and derivatives of this invention, taken alone or in admixture, can be used alone, or in a perfume composition as an olfactory component in detergents, soaps, space odorants and deodorants; perfumes; colognes, toilet waters; bath salts; hair preparations, such as lacquers, brilliantines, pomades and shampoos; cosmetic preparations, such as creams, deodorants, hand lotions, sunscreens; powders, such as talcs, dusting powders, face powders and the like; liquid bleaches, such as sodium hypochlorite-containing bleaches; floor waxes; automobile aromas and automobile polish compositions. When used as an olfactory component of a perfumed article, as little as 0.01% of one or more of the Prins reaction products of diisobutylene and derivatives of this invention will suffice to impart an interesting, herbaceous, piney and woody aroma. Generally, no more than 0.5% is required to impart such aromas, however, in view of the rather low cost of the Prins reaction products of diisobutylene and derivatives of this invention, up to 100% of the perfume composition can be one or more of the Prins reaction products of diisobutylene and derivatives of this invention.

In addition, the perfume composition can contain a vehicle or carrier for the Prins reaction products of diisobutylene and derivatives of this invention, alone, or with other ingredients. The vehicle can be a liquid such as a non-toxic alcohol such as ethanol, a glycol such as proplyene glycol, or the like. The carrier can be an absorbent solid, such as a gum or components for encapsulating the composition such as gelatin which can be used to form a capsule wall surrounding the perfume oil, as by means of coacervation.

Furthermore, one or more of the Prins reaction products or derivatives thereof prepared in accordance with the process of my invention are capable of supplying and/or potentiating certain flavor and aroma notes usually lacking in many smoking tobacco flavors and substitute tobacco flavors provided herein.

As used herein in regard to smoking tobacco flavors, the terms "alter" and "modify" in their various forms means "supplying or imparting flavor character or note to otherwise bland smoking tobacco, smoking tobacco substitutes, or smoking tobacco flavor formulations or augmenting the existing flavor characteristic where a natural flavor is deficient in some regard or supplementing the existing flavor impression to modify its quality, character or taste".

As used herein, the term "enhance" is intended to means the intensification (without change in kind of quality of aroma or taste) of one or more taste and/or aroma nuances present in the organoleptic impression of smoking tobacco or a smoking tobacco substitute or a smoking tobacco flavor.

My invention thus provides an organoleptically improved smoking tobacco product and additives therefor, as well as methods of making the same which overcome specific problems heretofore encountered in which specific desired oriental, fruity, rum-like and Turkish tobacco-like notes on smoking and prior to smoking in the main stream and in the side stream are created or enhanced and may be readily controlled and maintained at the desired uniform level regardless of variations in the tobacco components of the blend.

My invention further provides improved smoking tobacco additives and methods whereby various oriental, fruity, rum-like and Turkish tobacco notes prior to smoking and on smoking are imparted (in the main stream and in the side stream) to smoking tobacco products and may be readily varied and controlled to produce the desired uniform flavor characteristics.

In carrying out this aspect of my invention, I add to smoking tobacco materials or a suitable substitute therefor (e.g., dried lettuce leaves) an aroma and flavor additive containing as an active ingredient at least one Prins reaction product or Prins reaction product derivative prepared in accordance with the process of my invention.

In addition to the one or more Prins reaction products or Prins reaction product derivatives prepared in accordance with the process of my invention, other flavoring and aroma additives may be added to the smoking tobacco materials or substitute therefore either separately or in admixture with the one or more Prins reaction products or Prins reaction product derivatives prepared in accordance with the process of my invention as follows:

(i) Synthetic Materials

Beta-ethyl-cinnamaldehyde;
Beta-cyclohomocitral;
Eugenol;
Dipentene;
$\beta$-Damascenone;
$\beta$-Damascone;
Maltol;
Ethyl maltol;
Delta-undecalactone;
Delta-decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-one;
2-Methyl-5-isopropyl acetophenone;
2-Hydroxy-2,5,5,8a-tetramethyl-1-(2-hydroxyethyl)-decahydronaphthalene;
Dodecahydro-3a,6,6,9a-tetramethylnaphtho-[2,1,b]-furan;
4-Hydroxy hexanoic acid, gamma lactone; and
Polyisoprenoid hydrocarbons defined in Example V of U.S. Pat. No. 3,589,372 issued on June 29, 1971.

(ii) Natural Oils

Celery seed oil;
Coffee extract;
Bergamot Oil;
Cocoa extract;
Nutmeg oil;
Origanum oil An aroma and flavoring concentrate containing one or more Prins reaction products or Prins reaction product derivatives prepared in accordance with the process of my invention and, if desired, one or more of the above-identified additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as enhancement or the imparting of natural and/or sweet notes, I have found that satisfactory results are obtained if the proportion by weight of the sum total of one or more Prins reaction products or Prins reaction product derivatives produced to smoking tobacco material is between 250 ppm and 1,500 ppm (0.025%–0.15%) of the active ingredients to the smoking tobacco material. I have further found that satisfactory results are obtained if the proportion by weight of the sum total of one or more Prins reaction products or Prins reaction product derivatives prepared in accordance with the process of my invention is between 2,500 and 15,000 ppm (0.25%–1.50%).

Any convenient method for incorporating one or more Prins reaction products or Prins reaction product derivatives prepared in accordance with the process of my invention in the tobacco product may be employed. Thus, one or more Prins reaction products or Prins reaction product derivatives taken alone or along with other flavoring additives may be dissolved in a suitable solvent such as ethanol, pentane, diethyl ether and/or other volatile organic solvents and the resulting solution may be either sprayed on the cured, cased and blended tobacco material or the tobacco material may be dipped into such solution. Under certain circumstances, a solution containing one or more Prins reaction products or Prins reaction product derivatives prepared in accordance with the process of my invention taken alone or taken further together with other flavoring additives as set forth above may be applied by means of a suitable applicator such as a brush or roller on the paper or leaf wrapper for the smoking product, or it amy be applied to the filter by either spraying, or dipping, or coating.

Furthermore, it will be apparent that only a portion of the smoking tobacco or substitute therefor need be treated and the thus treated tobacco may be blended with other tobaccos before the ultimate tobacco product is formed. In such cases, the tobacco treated may have one or more Prins reaction products or Prins reaction product derivatives prepared in accordance with the process of my invention in excess of the amount or concentrations above indicated so that when blended with other tobaccos, the final product will have the percentage within the indicated range.

In accordance with one specific example of my invention, an aged,¹cured and shredded domestic Burley tobacco is sprayed with a 20% ethyl alcohol solution of substantially pure material produced according to Example II, being a mixture of compounds defined according to the structures:

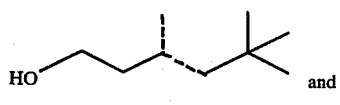 and 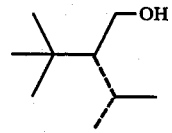

wherein in the mixture in each of the molecules one of the dashed lines represents a carbon-carbon double bond and the other of the dashed lines represents a carbon-carbon single bond in an amount to provide a tobacco composition containing 800 ppm by weight of said Prins reaction product derivative having the structures:

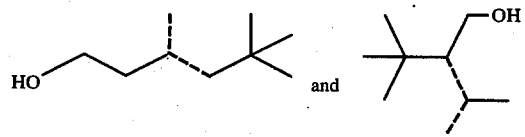

on a dry basis.

Thereafter, the alcohol is removed by evaporation and the tobacco is manufactured into cigarettes by the usual techniques. The cigarette, when treated as indicated, has a desired and pleasing aroma prior to smoking which can be described as fruity, oriental-like and rum-like and on smoking in the main stream and the side stream, a sweet, oriental-like, fruity, rum-like and Turkish tobacco-like aroma.

While my invention is particularly useful in the manufacture of smoking tobacco such as cigarette tobacco, cigar tobacco and pipe tobacco, other smoking tobacco products formed from sheeted tobacco dust or fines may also be used. Likewise one or more Prins reaction products or Prins reaction product derivatives prepared in accordance with the process of my invention can be incorporated with materials such as filter tip materials, seam paste, packaging materials and the like which are used along with tobacco to form a product adapted for smoking. Furthermore, one or more of the Prins reaction products or Prins reaction product derivatives prepared in accordance with the process of my invention can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco plant parts or substitute materials or both.

It will thus be apparent, that the Prins reaction products of diisobutylene and derivatives thereof of this invention can be utilized to alter, modify, augment or enhance sensory properties particularly organoleptic properties such as fragrances, and tases of a wide variety of consumable materials.

The following examples serve to illustrate out invention, and this invention is to be considered restricted thereto only as indicated in the appended claims.

All parts and percentages given herein are by weight unless otherwise specified.

EXAMPLE I

PREPARATION OF PRINS REACTION PRODUCT OF DIISOBUTYLENE

Reaction:

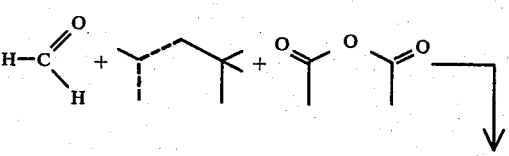

Reaction:

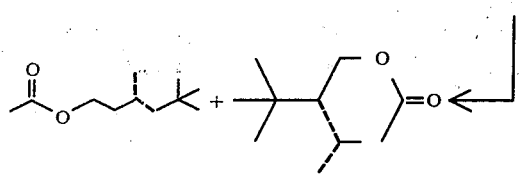

(wherein, in the resulting mixture, in each of the molecules of the mixture one of the dashed lines represents a carbon-carbon double bond, and the other of the dashed lines represents a carbon-carbon single bond).

Into a 5 liter, 3 neck flask equipped with 3 liter addition funnel, stirrer, thermometer and reflux condenser is placed 1428 ml acetic anhydride and 25 ml boron trifluoride etherate. The resulting mixture is heated to 40° C. and while maintaining the temperature at 70° C. over a period of 1 hour, a previously-prepared mixture of 324 grams of paraformaldehyde and 1600 ml diisobutylene is added to the reaction mixture. At the end of the 1 hour period, after addition is complete, the reaction mass is stirred with cooling for a period of 2 hours. At the end of the 2 hour period, with the reaction mass at 27° C., the reaction mass is poured into 1400 ml water. The reaction mass then separates into two phases; an organic phase and an aqueous phase. The organic phase is washed with one (1) liter portion of 10% aqueous sodium hydroxide, followed by water, whereby the pH of the resulting material is 3.5. The reaction mass is then distilled on a "2" stone packed column yielding the following fractions:

| Fraction Number | Vapor Temp. (°C.) | Liquid Temp. (°C.) | Pressure mm/Hg. | Weight of Fraction (g) |
|---|---|---|---|---|
| 1 | 77 | 89 | 4.0 | 249 |
| 2 | 76 | 90 | 3.5 | 396 |
| 3 | 87 | 114 | 3.5 | 347 |
| 4 | 135 | 172 | 3.5 | 288 |

The reaction mass is then subsequently distilled on a fractionation column yielding 15 fractions:

| Fraction Number | Vapor Temp. (°C.) | Liquid Temp. (°C.) | Pressure mm/Hg. | Weight of Fraction (g) |
|---|---|---|---|---|
| 1 | 28 | 90 | — | 86 |
| 2 | 78 | 96 | — | 82 |
| 3 | 43 | 97 | — | 76 |
| 4 | 39 | 94 | — | 66 |
| 5 | 40 | 96 | — | 38 |
| 6 | 44 | 94 | — | 56 |
| 7 | 44 | 93 | 0.9 | 82 |
| 8 | 41 | 98 | 0.6 | 84 |
| 9 | 48 | 104 | 0.9 | 91 |
| 10 | 43 | 108 | 0.7 | 88 |
| 11 | 42 | 115 | 0.6 | 76 |
| 12 | 43 | 128 | 0.7 | 74 |
| 13 | 55 | 160 | 0.7 | 39 |
| 14 | 130 | 163 | — | 16 |
| 15 | 123 | 230 | — | 108 |

Fractions 4–15 are bulked.

Figure 1:
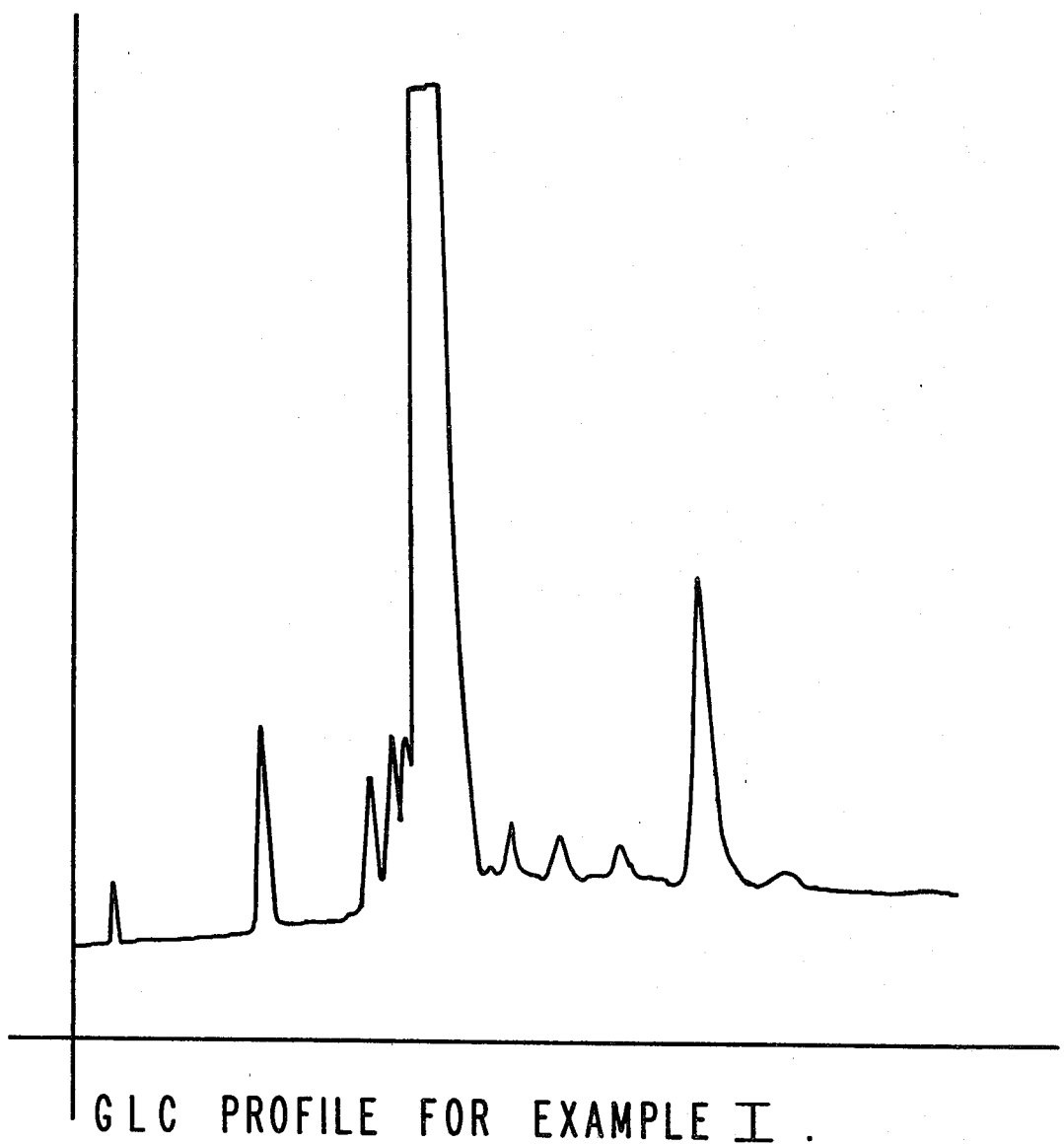
FIG. 1 is the GLC profile for the reaction product of Example I containing a mixture of compounds defined according to the structures.

FIG. 1 is the GLC profile for the reaction product prior to distillation.

FIG. 2 is the infra-red spectrum for the distillation product of the reaction product bulked fractions 4–15.

FIG. 3 is the NMR spectrum for the distillation product of the foregoing reaction product, bulked fractions 4–15.

EXAMPLE II

PREPARATION OF HYDROLYSIS PRODUCT OF PRINS REACTION PRODUCT OF DIISOBUTYLENE

Reaction:

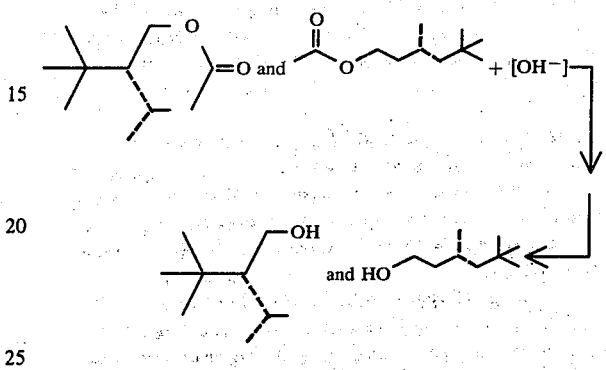

(wherein, in the resulting mixture, in one of the molecules of the mixture 1 of the dashed lines represents a carbon-carbon double bond, and the other of the dashed lines represents a carbon-carbon single bond).

Into a 1 liter reaction flask equipped with stirrer, thermometer and reflux condenser is placed:
(a) 208 grams of the Prins reaction product prepared according to Example I, bulked fractions 4–15 defined according to the generic structures:

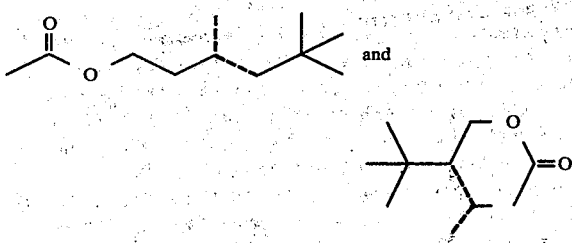

(wherein, in the mixture, in each molecule of the mixture, one of the dashed lines represents a carbon-carbon double bond and the other of the dashed lines represents a carbon-carbon single bond).
(b) 190 grams 50% aqueous sodium hydroxide
1 gram of Aliquat ®336 (quaternary ammonium salt; cetyl trimethyl ammonium chloride manufactured by the General Mills Chemical Company of Minneapolis, Minnesota)

The reaction mass is heated to a 100° C. for 4 hours, thus yielding two phases; an organic phase and an aqueous phase. The reaction mass is cooled to room temperature and placed in a separatory funnel. The organic phase is separated from the aqueous phase, and the aqueous phase is washed with 475 ml anhydrous diethyl ether. The ether is evaporated from the ether extract and combined with the organic phase. The resulting organic phases are washed with 375 ml portions of water. The organic phase is then washed as follows:
(a) One 500 ml portion of water;
(b) 475 ml portions diethyl ether;

(c) 375 ml portions water;
(d) 175 ml portions saturated salt.

The resulting organic phase is then dried over anhydrous magnesium sulfate, evaporated and distilled. One fraction results from the distillation boiling at 47° C. and 1.6 mm Hg. pressure. The yield is 91 grams.

FIG. 4 is a GLC profile of the reaction product prior to distillation.

FIG. 5 is the NMR spectrum of the distillation product of the reaction product of this example containing a mixture of compounds defined according to the generic structures:

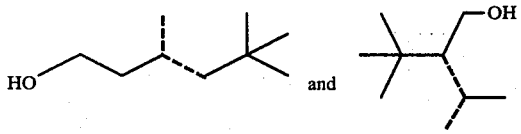

and wherein, the mixture in each of the molecules, one of the dashed lines represents a carbon-carbon double bond and each of the other of the dashed lines represents a carbon-carbon single bond.

EXAMPLE III

DILL SPICE FLAVOR

The following formulation is produced:

| Ingredients | Parts by Weight |
| --- | --- |
| Oil of dillweed | 84.5 |
| Oil of garlic | 1.75 |
| Oil of capsicum | 3.75 |
| Oil of cassia | 2.50 |
| Oil of cloves | 2.50 |
| Oil of pimenta berries | 2.50 |
| Oil of mustard | 1.25 |
| Oil of bay leaves | 1.25 |
| L-carvone | 4.60 |
| D-carvone | 3.80 |
| Cumin aldehyde | 2.51 |

The formulation is split into three parts. To one part is added the Prins reaction product mixture produced according to Example I, to the second part is added a derivative of the Prins reaction product mixture prepared according to Example II. To the third part, nothing is added. The three formulations are prepared at levels of 5 ppm, 10 ppm and 20 ppm in water and in tomato ketchup. The formulations containing the Prins reaction product of Example I and the Prins reaction product derivatives of Example II cause the flavor to be much more full bodied and more natural-like, as the flavor has cumin oil-like, and minty nuances in addition to the "natural" dill-like nuances. The "Natural" aspects of these flavors, together with the caraway-like, cumin oil-like and minty nuances are missing in the flavor that does not contain the Prins reaction product or the Prins reaction product derivatives produced according to either of Examples I or II.

EXAMPLE IV

SPEARMINT FLAVOR

The following spearment flavor is produced.

| Ingredients | Parts by Weight |
| --- | --- |
| Spearmint oil | 42.0 |
| L-carvone | 12.0 |
| D-carvone | 8.0 |

This formulation is split into three portions. To the first portion and to the second portion, 4.0 parts by weight, respectively, of the Prins reaction products and Prins reaction product derivatives prepared according to Examples I and II, respectively, are added. To the third portion, nothing is added. The flavors are tested at levels of 5 ppm, 10 ppm and 20 ppm in water and in chewing gum which heretofore was unflavored. The chewing gum containing the flavor formulations with the Prins reaction product derivatives and Prins reaction products produced according to Examples I and II have more natural-like, minty aromas and tastes, with excellent and caraway and dill-like nuances present. The formulations have great amounts of "natural mintiness" which are not only "natural-like" but which are also "long lasting" and which remain of high strength throughout the chewing procedure of the chewing gums.

EXAMPLE V

A toothpaste is prepared according to the following formula:

| Ingredients | Parts by Weight |
| --- | --- |
| Sorbitol (70% soln.) | 20.00 |
| Sodium saccharin | 0.21 |
| Veegum (colloidal magnesium aluminum silicate) | 0.40 |
| Precipitated urea/formaldehyde condensate (abrasive) | 30.00 |
| Prins reaction product or Prins reaction product derivatives prepared according to Example I or II, respectively | 1.00 |
| Sodium carboxymethycellulose | 1.30 |
| Glycerine | 10.00 |
| 1,2-bis($N^5$—p-chlorophenyl-$N^1$—biguanido) ethane digluconate | 0.70 |
| Polyoxyethylene sorbitan (20) monoisostearate | 1.50 |
| Distilled water | balance to 100 |

This toothpaste when used in the normal manner, is not only effective in retarding the formation of dental plaque and produce appreciably lower levels of strain on the teeth than does chlorhexidine; but, in addition, has an excellent sweet, spicy, minty, herbaceous, bread-like, caraway-like, cumin-like and dill-like taste profiles.

EXAMPLE VI

A mouthwash in accordance with the present invention is formulated as follows:

| Ingredients | Parts by Weight |
| --- | --- |
| Ethyl alcohol (95% in water) | 12.00 |
| Cetyl pyridinium chloride | 0.10 |
| Polyoxyethylene (20) sorbitan monooleate | 0.12 |
| Sodium hydroxide (10% in water) | 0.02 |
| Sodium saccharin | 0.055 |
| Prins reaction product or Prins reaction product derivative prepared according to Example I or II, respectively | 0.16 |
| 1,2-bis($N^5$—p-chlorophenyl-$N^1$— |  |

| Ingredients | Parts by Weight |
|---|---|
| biguanido) ethane dihydrochloride | 0.20 |
| Color | 0.50 |
| Sorbitol (70% in water) | 12.00 |
| Distilled water | balance to 100 |

When used in the normal manner to rinse the mouth, these products are effective not only in retarding the formation of dental plaque and produce an apprecibly lower level of stain on the teeth than does chlorohexidine; but also have excellent sweet, spicy, minty, cumin-like, herbaceous, bread-like, caraway-like and dill-like taste profiles.

EXAMPLE VII

Chewing gum in accordance with the present invention are formulated as follows:

| Ingredients | Parts by Weight |
|---|---|
| Gum base | 21.30 |
| Ester Gum | 6.40 |
| Coumarone resin | 9.60 |
| Dry latex rubber | 3.20 |
| Paraffin wax (M.P. 180° F.) | 2.10 |
| Sugar | 58.45 |
| Corn syrup (Baume 45) | 18.20 |
| Prins reaction product or Prins reaction product derivatives prepared according to Example I or II, respectively | 1.5 |
| 1,2-bis($N^5$—p-chlorophenyl-$N^1$—biguanido) ethane diacetate | 1.00 |

Chewing these gums in the normal manner not only retards the formation of dental plaque and produce appreciably less staining on the teeth than does chlorhexidine but also gives rise to a pleasant, long-lasting and intense sweet, cumin-like, spicy, minty, herbaceous, bread-like, caraway-like and dill-like taste profile.

EXAMPLE VIII
CITRUS COLOGNES

The following citrus cologne formulations are prepared:

| Ingredients | Parts by Weight |
|---|---|
| Mixture of Prins reaction product defined according to the generic structure: 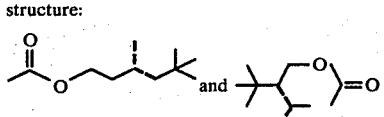 prepared according to Example I, wherein in the mixture one of the dashed lines represents a carbon-carbon double bond and the other of the dashed lines represents a carbon-carbon single bond: | 600 | or

| Ingredients | Parts by Weight |
|---|---|
| Mixture of products prepared according to Example II defined according to the structures: 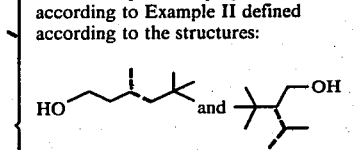 wherein, in the mixture, one of the dashed lines represents a carbon-carbon double bond and each of the other dashed lines represent a carbon-carbon single bond: | 600 |
| Bergamot Oil | 100 |
| Phenyl ethyl alcohol | 100 |
| Hydroxy citronella | 100 |
| Benzyl salicylate | 100 |

The Prins reaction products produced according to Examples I or II, impart to this citrus cologne formulation an excellent intense long-lasting spicy and clove and cinnamon-like and minty nuance with excellent warm woody undertones, in addition to the intense citrusy nuance already present in the citrus cologne formulation.

EXAMPLE IX

The Prins reaction products produced according to Examples I and II have excellent spicy, clove, cinnamon-like and minty aromas becoming strongly vetiver on dry-out. These aroma nuances may be utilized to a great extent in inexpensive functional products. The following pine fragrance demonstrates the use of this material in perfume compositions. In this case, each of the materials in Examples I or II are used at a rate of 47.9%.

| Ingredients | Parts by Weight |
|---|---|
| One of the Prins reaction products or Prins reaction product derivatives produced according to Examples I or II defined according to the generic structure: 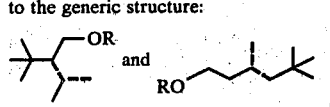 (wherein, in the mixture, one of the dashed lines represents a carbon-carbon single bond or a carbon-carbon double bond and "R" represents hydrogen or acetyl). | 479 |
| Isobornyl acetate | 100 |
| Camphor | 10 |
| Terpineol | 25 |
| Fir balsam absolute (50% in diethyl phthalate) | 20 |
| Coumarin | 4 |
| Linalool | 30 |
| Anethol | 2 |
| Fenchyl alcohol | 10 |
| Lemon terpenes washed | 50 |
| Borneol | 5 |
| Galbanum oil | 5 |
| Turpentine Russian | 150 |
| Pinus pumilionus | 50 |
| Eucalyptol | 50 |

| Ingredients | Parts by Weight |
|---|---|
| 2,2,6-trimethyl-1-cyclohexene-1-carboxaldehyde | 5 |
| Maltol 1% in diethyl phthalate | 5 |

The presence of the Prins reaction product and the Prins reaction product derivatives prepared according to Examples I or II, support the pine notes and impart strong, clove-like and spicy character, with cinnamon-like, floral, minty and warm woody nuances, particularly on dry-out to this formulation, thus producing a considerable savings in the cost of the formulation.

EXAMPLE X

PREPARATION OF COSMETIC POWDER COMPOSITIONS

Cosmetic powder compositions are prepared by mixing in a mill, 100 grams of talcum powder with 0.25 grams of each of the substances setforth in Table I per composition. Each of the cosmetic powder compositions has an excellent aroma as described in Table I below:

TABLE I

| Substance | Aroma Description |
|---|---|
| Mixture prepared according to Example I containing compounds defined according to the structures: 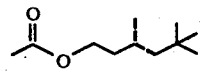 and 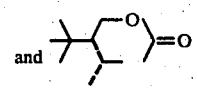 wherein, in the mixture in each of the molecules, one of the dashed lines represents a carbon-carbon double bond and the other of the dashed lines represents a carbon-carbon single bond. | A spicy, clove aroma with warm woody undertones. |
| Mixture prepared according to Example II containing the compounds defined according to the structures: 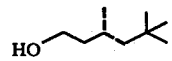 and 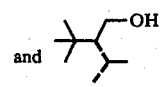 wherein, in each of the molecules of the mixture one of the dashed lines is a carbon-carbon double bond and the other of the dashed lines is a carbon-carbon single bond. | A spicy, cinnamon-like, floral and minty aroma. |
| Perfume composition of Example VIII. | A citrusy aroma with spicy, clove, cinnamon-like, floral and minty nuances. |
| Perfume compositions of Example IX. | A piney aroma having spicy, clove, cinnamon-like, floral, minty and vetiver nuances becoming piney/vetiver-like/warm woody |

TABLE I-continued

| Substance | Aroma Description |
|---|---|
| | on dry-out. |

EXAMPLE XI

PERFUMED LIQUID DETERGENTS

Concentrated liquid detergents (Lysine sale of n-dodecylbenzene sulfonic acid as more specifically described in U.S. Pat. No. 3,948,818, issued on April 6, 1976) with aroma nuances as set forth in Table II of Example X, are prepared containing 0.10%, 0.15%, 0.20%, 0.25%, 0.30% and 0.35% of the substance set forth in Table I of Example X. They are prepared by adding and homogeneously mixing the appropriate quantity of substance set forth in Table I of Example X below in the liquid detergent. The detergents all possess excellent aromas as set forth in Table I of Example X, the intensity increasing with greater concentrations of substance as set forth in Table I of Example X.

EXAMPLE XII

PREPARATION OF COLOGNES AND HANDKERCHIEF PERFUMES

Compositions as set forth in Table I of Example X are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table I of Example X are imparted to the colognes and to the handkerchief perfumes at all levels indicated.

EXAMPLE XIII

PREPARATION OF SOAP COMPOSITIONS

One hundred grams of soap chips [per sample] (Ivory ®, produced by the Procter & Gamble Company of Cincinnati, Ohio), are each mixed with one gram sample of substances as set forth in Table I of Example X until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table I of Example X.

EXAMPLE XIV

PREPARATION OF SOLID DETERGENT COMPOSITIONS

Detergents are prepared using the following ingredients according to Example I of Canadian Pat. No. 1,007,948:

| Ingredient | Percent by Weight |
|---|---|
| "Neodol ® 45-11 (a C$_{14}$–C$_{15}$ alcohol ethoxylated with 11 moles of ethylene oxide | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table I of Example X. Each of the detergent samples has an excellent aroma as indicated in Table I of Example X.

EXAMPLE XV

Utilizing the procedure of Example I at column 15 of U.S. Pat. No. 3,632,396, nonwoven cloth substrates useful as dry-added fabric softening articles of manufacture are prepared wherein the substrate, the substrate coating and the outer coating and the perfuming material are as follows:
1. A water "dissolvable" paper ("Dissolvo Paper")
2. Adogen 448 (m.p. about 140° F.) as the substrate coating; and
3. An outer coating having the following formulation (m.p. about 150° F.):
57% $C_{20-22}$ HAPS
22% isopropyl alcohol
20% antistatic agent
1% of one of the substances as set forth in Table I of Example X Fabric softening compositions prepared according to Example I at column 15 of U.S. Pat. No. 3,632,396 having aroma characteristics as set forth in Table I of Example X, consist of a substrate coating having a weight of about 3 grams per 100 square inches of substrate; a first coating on the substrate coating consisting of about 1.85 grams per 100 square inches of substrate; and an outer coating coated on the first coating consisting of about 1.4 grams per 100 square inches of substrate. One of the substances of Table I of Example X is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said dryer-added fabric softener non-woven fabrics and these aroma characteristics are described in Table I of Example X.

EXAMPLE XVI

HAIR SPRAY FORMULATIONS

The following hair spray formulation is prepared by first dissolving PVP/VA E-735 copolymer manufactured by the GAF Corporation of 140 West 51st Street, New York, N.Y., in 91.62 grams of 95% food grade ethanol. 8.0 grams of the polymer is dissolved in the alcohol. The following ingredients are added to the PVP/VA alcoholic solution:
Dioctyl sebacate—0.05 weight percent
Benzyl alcohol—0.10 weight percent
Dow Corning 473 fluid (prepared by the Dow Corning Corporation)—0.10 weight percent
Tween 20 surfactant (perpared by ICI America Corporation)—0.03 weight percent
One of the perfumery substances as set forth in Table I of Example X—0.10 weight percent The perfuming substances as set forth in Table I of Example X add aroma characteristics as set forth in Table I of Example X which are rather intense and aesthetically pleasing to the users of the soft-feel, good-hold pump hair sprays.

EXAMPLE XVII

CONDITIONING SHAMPOOS

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.).

Gafquat®755 N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation.

The resulting material is then mixed and cooled to 45° C. and 0.3 weight percent of perfuming substance as set forth in Table I of Example X is added to the mixture. The resulting mixture is cooled to 40° C. and blending is carried out for an additional one hour in each case. At the end of this blending period, the resulting material has a pleasant fragrance as indicated in Table I of Example X.

What is claimed is:
1. A process for augmenting or enhancing the aroma of a perfume composition or cologne comprising the step of adding to a perfume composition or cologne base an aroma augmenting or enhancing quantity of a compound defined according to the structure:

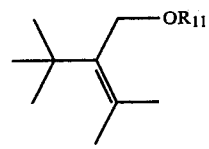

wherein $R_{11}$ represents hydrogen or acetyl.
2. The process of claim 1 wherein $R_{11}$ is hydrogen.
3. The process of claim 1 wherein $R_{11}$ is acetyl.

* * * * *